United States Patent

Prezewowsky et al.

[11] 3,951,959
[45] Apr. 20, 1976

[54] 1,3-OXYGENATED 8α-ESTRATRIENES

[75] Inventors: Klaus Prezewowsky; Henry Laurent; Helmut Hofmeister; Rudolf Wiechert; Friedmund Neumann; Yukishige Nishino, all of Berlin, Germany

[73] Assignee: Schering Aktiengesellschaft, Berlin & Bergkamen, Germany

[22] Filed: July 12, 1974

[21] Appl. No.: 488,058

[52] U.S. Cl. .................... 260/239.55 R; 260/397.4; 260/397.5; 260/239.5
[51] Int. Cl.² .................... C07J 43/00; C07J 1/00
[58] Field of Search .............................. 260/397.5

[56] References Cited
UNITED STATES PATENTS
3,686,238   8/1972   Zaffaroni .......................... 260/399
FOREIGN PATENTS OR APPLICATIONS
1,128,254   9/1968   United Kingdom .............. 260/397.5
1,208,039   10/1970   United Kingdom .............. 260/397.5

OTHER PUBLICATIONS
"Steroids," Vol. 66, (1967), Par. 65.722u.

Primary Examiner—Elbert L. Roberts
Attorney, Agent, or Firm—Millen, Raptes & White

[57] ABSTRACT

8α-Estratrienes of the formula

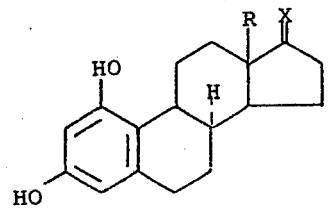

wherein R is lower alkyl and X is an oxygen atom, a β-hydroxy or β-hydroxy-α-substituted or unsubstituted saturated or unsaturated hydrocarbon group, and the esters and ethers thereof, possess strong vaginotropic but only weak utertropic activity and are useful in the treatment of estrogenic deficiency conditions where uteral effects are not desired.

24 Claims, No Drawings

1,3-OXYGENATED 8α-ESTRATRIENES

BACKGROUND OF THE INVENTION

This invention relates to novel 8α-estratrienes.

SUMMARY OF THE INVENTION

In a composition aspect, this invention relates to 1,3-oxygenated 8α-estratrienes of the general Formula I

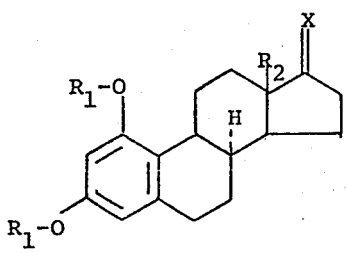

wherein X is an oxygen atom or the group

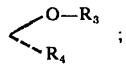

$R_1$ and $R_3$ each are a hydrogen atom, acyl, alkyl, cycloalkyl, or an oxygen-containing saturated heterocyclic group; $R_2$ is lower alkyl; $R_4$ is a hydrogen atom or a substituted or unsubstituted, saturated or unsaturated hydrocarbon group.

In another composition aspect, this invention relates to pharmaceutical compositions comprising a vaginotropic effective amount of a compound of this invention in admixture with a pharmaceutically effective carrier.

DETAILED DISCUSSION

Suitable acyl groups are those of any physiologically acceptable acid, including sulfonic and carboxylic acids. Preferred acyl groups are those of hydrocarbonic carboxylic acids and sulfonic acids of 1-15 carbon atoms, including those of the aliphatic, cycloaliphatic, aromatic, aromaticaliphatic series. Equivalent of these are those of the heterocyclic series and those which are unsaturaated and/or polybasic and/or substituted in the usual manner, e.g., by alkyl, hydroxy, alkoxy, oxo, or amino groups, or halogen atoms.

Examples of suitable carboxylic acids ar alkanoic acids of 1-15, preferably 2-8 carbon atoms, e.g., formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert.-butylacetic acid, and cycloalkylalkanoic acids wherein cycloalkyl and alkanoic are as defined herein, e.g., cyclopentylacetic acid, cyclohexylacetic acid, cyclohexanecarboxylic acid and aryl cabocyclic carboxylic and aryl carbocyclicalkanoic acids of 7-15, preferably 7-12, carbon atoms, e.g., benzoic and phenylacetic acid. Equivalents of these acids are, e.g., phenoxyacetic acid, mono-, di-, and trichloroacetic acid, aminoacetic acid, diethylaminoactic acid, piperidinoacetic acid, morpholinoacetic acid, lactic acid, succinic acid, adipic acid, benzoic acid, nicotinic acid, isonicotinic acid, furan-2-carboxylic acid.

Examples of sulfonic acids are alkanesulfonic acids of 1-6 carbon atoms, e.g., methanesulfonic acid, ethanesulfonic acid, butanesulfonic acid, cycloalkanesulfonic acids of 3-8 carbon atoms, e.g., cyclopentanesulfonic acid and cyclohexanesulfonic acid, and aryl carbocyclicsulfonic acids of 6-12 carbon atoms, e.g., benzenesulfonic acid and p-toluenesulfonic acid. Examples of equivalents of these acids are β-chloroethanesulfonic acid, p-chlorobenzenesulfonic acid, N,N-dimethylaminosulfonic acid, N,N-diethylaminosulfonic acid, N,N-bis(β-chloroethyl)aminosulfonic acid, N,N-diisobutylaminosulfonic acid, N,N-dibutylaminosulfonic acid, pyrrolidino-, piperidino-, piperazino-, N-methylpiperazino-, and morpholinsulfonic acid.

Preferred $R_1$ or $R_3$ alkyl groups are lower alkyl of 1-5 carbon atoms, which can be branched in the usual manner. Especially preferred are methyl and ethyl. Equivalents are those substituted in the usual manner, e.g., by a halogen atom, preferably chlorine, or lower alkoxy, preferably methoxy.

Examples of cycloalkyl groups are those of 3-8 carbon atoms, e.g., cyclopentyl, cyclopropyl, cyclohexyl, cycloheptyl and the corresponding rings bearing, e.g., 1-3 alkyl, preferably methyl, groups. Cyclopentyl group is preferred.

An example of a saturated oxygen-containing heterocyclic group is tetrahydropyranyl, which is preferred. Equivalent are any other such groups derived from heterocycles of at least one oxygen atom in the ring and which are perhydrogenated in the oxygen-containing ring, e.g., tetrahydrofuryl.

Examples of hydrocarbon $R_4$ groups are saturated and mono-unsaturated hydrocarbon of up to 6 carbon atoms, viz., alkyl, alkenyl and alkinyl, e.g., methyl, ethyl, propyl, butyl, pentyl, hexyl, vinyl, ethinyl and propenyl. Equivalents are di-unsubstituted groups, e.g., butadienyl, butadiynyl and the corresponding hydrocarbon groups bearing the usual substituents, e.g., halogen, preferably chloro. Preferred hydrocarbon and substituted hydrocarbon groups are ethinyl and chloroethinyl, respectively.

Examples of $R_2$ are lower alkyl groups of 1-4 carbon atoms, e.g., methyl, ethyl, propyl, and butyl, preferably methyl or ethyl.

Preferred classes of compounds of this invention are those wherein:

a. X is

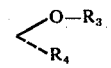

and $R_1$ and $R_3$ are alike or different and are hydrogen atoms, alkyl of 1-4 carbon atoms, preferably methyl, or alkanoyl of 2-8 carbon atoms, preferably acetyl; and $R_4$ is a hydrogen atom or when $R_3$ is a hydrogen atom, ethinyl;

b. those of (a) wherein $R_1$ and $R_3$ are alike, especially those wherein $R_4$ is a hydrogen atom; and c. those of (b) wherein $R_1$ is alkanoyl or alkyl, preferably acetyl or methyl.

The compounds of this invention have an advantageous dissociated pharmacological activity, viz., strongly vaginotropic and weakly uterotropic effectiveness, they are preferably suitable for the treatment of estrogen deficiency where an estrogenic effect on the vaginal epithelium is desired, but an estrogenic effect on the uterus is to be avoided is possible. For example, they are suitable for the treatment of females in the postmenopausal period, e.g., climacteric and its sequelae, deficiency symptoms following ovarectomy and radiological castration, osteoporosis, depressive mood, perpheric circulatory disorders, cardiac diseases and senile otosclerosis.

The compounds of this invention are also useful as intermediates for the preparation of other pharmacologically useful steroids.

The favorable estrogenic dissociation can be shown, for example, in the sialic acid test on mice. The sialic test is conducted as follows:

The mice are ovariectomized. Starting with the 10th day after castration, the animals receive the substance to be tested once daily for 3 days. On the fourth day, the animals are sacrificed. Vagina and uterus are immediately excised and weighed into a test tube for hydrolysis. The determination of the sialic acid is conducted according to Svennerholm [Biochem. Biophys. Acta 24 (1957) 604]. The increase in the organ weights of vagina and uterus in dependence on the dose, as well as the reduction in the sialic acid content are determined, deriving therefrom the relative effective strength of the compound to be tested compared to the standard, estradiol (II). The relative effectivenesses are converted into a ratio and result in the degree of dissociation, Q. For the standard compound estradiol, Q = 1. Compounds with Q > 1 are primarily vaginotropic, and with Q < 1 are primarily uterotropic.

The threshold values indicated in Table 1 were determined on rats in the usual Allen-Doisy test.

In this test, the compounds of this invention exhibit a dissociation quotient for surpassing that of the standard compounds, as shown in Table 1, in which the standard estrogens, 17α-ethinyl-1,3,5(10)-estratriene-3,17β-diol (I) and 1,3,5(10)-estratriene-3,17β-diol (II), are compared with the compounds of this invention, 1,3,17β-triacetoxy-8α-estra-1,3,5(10)-triene (III),
1,3,diacetoxy-8α-estra-1,3,5(10)-trien-17β-ol (IV),
1,3-diacetoxy-8α-estra-1,3,5(10)-trien-17-one (V),
1,3-dimethoxy-8α-estra-1,3,5(10)-trien-17-one (VI),
1,3-dicyclopentyloxy-8α-estra-1,3,5(10)-trien-17-one (VII),
1,3-dihydroxy-8α-estra-1,3,5(10)-trien-17-one (VIII),
1,3-dimethoxy-17α-ethinyl- 8α-estra-1,3,5(10)-trien-17β-ol (IX),
1,3-diacetoxy-17α-ethinyl-8α-estra-1,3,5(10)-trien-17β-ol (X), and
1,3-dimethoxy-8α-estra-1,3,5(10)-trien-17β-ol (XI).

TABLE 1

| No. | Name | Threshold Value [mg.] | | Dissociation Quotient | |
|---|---|---|---|---|---|
| | | s.c. | p.o. | s.c. | p.o. |
| I | 17α-Ethinyl-1,3,5(10)-estratriene-3,17β-diol | 0.0003 | 0.01 | 0.4 | 0.8 |

TABLE 1-continued

| No. | Name | Threshold Value [mg.] | | Dissociation Quotient | |
|---|---|---|---|---|---|
| | | s.c. | p.o. | s.c. | p.o. |
| II | 1,3,5(10)-Estratriene-3,17β-diol | 0.0005 | 0.05–0.1 | 1.0 | 1.0 |
| III | 1,3,17β-Triacetoxy-8α-estra-1,3,5(10)-triene | 0.03 | | 4.0 | 3.7 |
| IV | 1,3-Diacetoxy-8α-estra-1,3,5-(10)-trien-17β-ol | 0.03 | | 7.0 | 6.0 |
| V | 1,3-Diacetoxy-8α-estra-1,3,5-(10)-trien-17-one | 0.03 | 0.03–0.1 | 4.0 | 2.0 |
| VI | 1,3-Dimethoxy-8α-estra-1,3,5(10)-trien-17-one | 0.1–0.3 | | 2.3 | |
| VII | 1,3-Dicyclopentyloxy-8α-estra-1,3,5(10)-trien-17-one | | | 2.3 | |
| VIII | 1,3-Dihydroxy-8α-estra-1,3,5-(10)-trien-17-one | 0.1 | | 3.2 | |
| IX | 1,3-Dimethoxy-17α-ethinyl-8α-estra-1,3,5(10)-trien-17β-ol | 0.1 | 0.3 | 3.2 | |
| X | 1,3-Diacetoxy-17α-ethinyl-8α-estra-1,3-5(10)-trien-17β-ol | 0.003 | 0.3 | 1.8 | 2.0 |
| XI | 1,3-Dimethoxy-8α-estra-1,3-5(10)-trien-17β-ol | 0.1–0.3 | 0.1 | 2.5 | 2.3 |

This invention also relates to pharmaceutical compositions comprising an 8α-estratriene of general Formula I in admixture with a pharmaceutical carrier.

Such compositions are produced in the usual manner by formulating the effective agents into the desired forms of application, e.g., tablets, dragees, capsules, oral and injectable solutions, employing the usual vehicles, diluents, flavor-ameliorating agents, etc. customary in galenic pharmacy.

The effective agent concentrations in the thus-formulated drugs is dependent on the mode of administration. Thus, a tablet preferably contains 0.01 - 10 mg.; solutions for parenteral administration preferably contain 0.1 - 20 mg./ml. of solution.

As will be apparent to those skilled in the art, the dosage of the medicinal agents of this invention can vary with the type of administration and the respectively selected compound. Moreover, the dosage can vary from patient to patient. In general, the compounds of the present invention are administered at a dosage level which can achieve the desired results without causing any disadvantageous or deleterious side effects. Thus, the compounds are administered, for example, at a dosage level ranging from approximately 0.02 mg. to about 20 mg., although modifications can be made under certain circumstances, so that a dosage level or more than 20 mg., for example up to 50 mg., is employed. However, a dosage level in the range of about 0.05 mg. to approximately 5 mg. is preferred.

The compounds of general Formula I can be prepard by hydrogenating, in a conventional manner, an estra-oligo-ene of the general Formula II

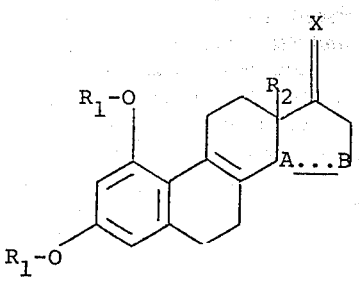

II wherein $R_1$, $R_2$, and X have the values given above and A⋯B is a single or double bond, and optionally thereafter reducing the 17-keto group and/or splitting off ether or acyl groups and/or esterifying and/or etherifying free hydroxy groups, depending on the finally desired values for X and $R_1$.

The compounds of general Formula I can also be produced by oxidizing a 3-hydroxy-13-$R_2$-8α-estra-1,3,5(10)-trien-17-one wherein $R_2$ has the values given above with lead tetraacylate, rearranging the reaction product in the presence of a strong acid, and optionally subsequently reducing the 17-keto group and/or splitting off ether or acyl groups and/or esterifying and/or etherifying free hydroxy groups, depending on the finally desired values for X and $R_1$.

The novel compounds are produced according to methods known per se.

The hydrogenation of the estra-oligo-enes of Formula II can be accomplished, for example, by catalytic hydrogenation. Suitable catalysts are, inter alia, heavy metal catalysts, such as palladium, optionally distributed on supports, e.g., calcium carbonate, activated carbon, or barium sulfate, or Raney nickel. During the hydrogenation, if unsaturated hydrocarbon $R_4$ group is present in the molecule, it can also be partially hydrogenated. If a compound wherein $R_4$ is unsaturated hydrocarbon group is the desired final compound, it is advantageous first to carry out the hydrogenation on a compound of Formula II wherein X is an oxygen atom, and then follow this step by the reduction with an organometallic compound wherein the orgaic group is the desired $R_4$ unsaturated hydrocarbon group.

The oxidation with lead tetraacetate and the subsequent rearrangement in the presence of acid is known from the literature for 3-hydroxy-8β-estra-1,3,5(10)-trienes, but could not be applied to the corresponding 3-hydroxy-8α-estratrienes [Rufer et al., Liebigs Ann. Chem. [Liebig's Annals of Chemistry] 752 (1971) 5]. In contrast to Rufer et al., the reaction can be accomplished if the oxidation is conducted with lead tetraacylate in the usual manner but terminating the reaction after a short period of time, for example after three minutes. The reaction product is then worked up and rearranged in the conventional manner.

A 17-keto group can be subsequently reduced, and for this purpose, several conventional methods are available.

For example, the reduction can be carried out by reaction with hydrogen in the presence of a customary catalyst, e.g., Raney nickel in benzene. The hydrogen can also be transferred to the 17-keto group from metal hyrides. Suitable hydrogen donors are, in particular, complex hydrides, e.g., sodium hydridoborate, lithium hydridoaluminate, sodium hydridotrimethoxoborate and lithium hydrido- tri-tert.-butoxoaluminate.

The reduction can also be carried out according to conventional methods with an organometallic compound whose organic group is the desired $R_4$ group, e.g., an alkylmagnesium halide, such as, for example, methylmagnesium bromide or iodide, an alkenylmagnesium and/or alkenylzinc halide, e.g., vinylmagnesium bromide or allylmagnesium bromide, an alkinylmagnesium halide, such as ethinylmagnesium bromide, propinylmagnesium bromide, or propinylzinc bromide, or an alkali metal acetylide, such as potassium acetylide. The organometallic compound utilized as the reducing agent can also be formed in situ and made to react with the 17-ketone of Formula II. Thus, for the reaction with organometallic alkinyl compounds, the ketone is treated, in a suitable solvent, with an alkine, a chloroalkine, or alkadyine, and an alkali metal, preferably in the presence of a tertiary alcohol or ammonia, optionally under elevated pressure.

Free hydroxy grops can subsequently be esterified or etherified. Esterified or etherified hydroxy groups can be converted into the hydroxy groups.

The acylation at the 1- and 3-positions is preferably conducted with pyridine and the selected acid anhydride and/or pyridine/acid chloride at room temperature. For etherification in the 1- and 3-positions, alkylating compounds are employed, preferably diazomethane, dialkyl sulfates, cycloalkyl halogenides or dihydropyran.

For the esterification of the 17β-hyroxy group in 1,3-diesters and 1,3-diethers, the steroid is treated, for example, with an acid anhydride in the presence of a strong acid, e.g., p-toluenesulfonic acid, $HClO_4$, or pyridine/acid anhydride, with heating. The last-mentioned methods can also be utilized to convert the free trihydroxy compound directly into the triacylate. From the triacylates, the 1- and 3-OH-groups can be liberated by gentle partial saponification.

1,3-Diesters and 1,3-diethers can be converted into the corresponding 17-tetrahydropyranyl ethers with dihydropyran in the presence of a strong acid, e.g., p-toluenesulfonic acid. The etherification of the 17-OH-group in the 1,3-diethers of this invention having an alkyl residue is conducted preferably with alkyl halogenides in liquid ammonia. The two last-mentioned methods also make it possible to etherify all OH-groups of the hydroxy compounds of this invention in a single process step.

The free 1- and 3-OH-groups can be liberated from 1,3-diacyl-17-tetrahydropyranyl derivatives by alkaline saponification.

The ether splitting step is conducted according to conventional methods. Examples of such processes are the splitting with pyridinehydrochloride or pyridine/concentrated hydrochloric acid at an elevated temperature (180°–220° C.) or with hydrohalic acids in the presence of lower carboxylic acids at temperatures of below 150° C., and the splitting of tetrahydropyranyl ethers, carried out under gentle conditions by the addition of an acid.

In order to increase the yield, it can be advantageous to start with compounds wherein the hydroxy groups in the 1- and 3-positions are esterified or etherified. For example, if the ether residues are introduced merely as intermediary masking groups, it is advantageous to carry out the etherification with dihydropyran, because these residues can later be split off especially readily.

The reduction can also be conducted while retaining ester groups present in he starting compound. On the other hand, hydroxy groups liberated during the reaction can be selectively reacylated in the 1-and/or 3- positions.

3-Hydroxy-8α-estra-1,3,5(10)-trien-17-ones are known from the literature. The other starting compounds can be produced as described by the following examples, using 1,3-dimethoxy-1,3,5(10),8,14-estrapentaen-17-one (A),
1,3-dimethoxy-17β-acetoxy-1,3,5(10),8,14-estrapentaene (B), and
1,3-dimethoxy-17β-acetoxy-1,3,5(10),8-estratetraene (C).

PREPARATIONS

A:
1,3-Dimethoxy-1,3,5(10),8,14-estrapentaen-17-one

A trace of iodine and 2 ml. of ethyl bromide are added to a suspension of 17 g. of Mg filings in 15 ml. of absolute THF; after heating the mixture to 50° C., vinyl chloride is gradually introduced until the temperature has dropped to room temperature. During this introduction, 250 ml. of absolute THF is added dropwise. At 20° C., a solution of 52.4 g. of 6,8-dimethoxytetralone in 84 ml. of absolute THF and 82 ml. of absolute benzene is gradually fed dropwise into this vinyl Grignard solution, and the mixture is allowed to stand overnight in the refrigerator under a nitrogen atmosphere. After heating to room temperature, the mixture is introduced into 84 ml. of glacial acetic acid and 350 ml. of ice water, combined with each other; the mixture is agitated for 30 minutes, the aqueous phase is separated and extracted with benzene. The combined organic extracts are washed neutral with $NaHCO_3$ solution and water and then dried. This solution of the vinol compound is combined with 38 g. of 2-methylcyclopentanedione-(1,3) and 160 mg. of potassium hydroxide (pulverized); the mixture is concentrated to one-half thereof, and 170 ml. of methanol is gently added thereto. The mixture is then heated to the boiling point for 3 hours under $N_2$, cooled to room temperature, diluted with ether, and the excess 2-methylcyclopentanedione-(1,3) is removed by extraction with 10% strength sodium hydroxide solution. After washing the mixture neutral with water, drying, and evaporation, the product is recrystallized from ethanol, thus obtaining 66 g. of 1,3-dimethoxy-8,14-seco-1,3,5(10),9(11)-estratetraene-14,17-dione, m.p. 87/88°–89° C.

A solution of 69 g. of 1,3-dimethoxy-8,14-seco-1,3,5(10),9(11)-estratetraene-14,17-dione in 940 ml. of distilled benzene is mixed with 3 g. of p-toluenesulfonic acid and heated to the boiling point for 20 minutes. After cooling, the mixture is extracted with cold $NaHCO_3$ solution, washed neutral with water, and dried. After recrystallization from acetone/hexane over carbon, 60 g. of rac.-1,3-dimethoxy-1,3,5(10),8,14-estrapentaen-17-one, m.p. 120°–121°C.

B:
1,3-Dimethoxy-17β-acetoxy-1,3,5(10),8,14-estrapentaene

A solution of 60 g. of rac.-1,3-dimethoxy-1,3,5(10),-8,14-estrapentaen-17-one in 2.4 l. of methanol and 1.0 l. of THF is gradually combined at room temperature with 6.0 g. of $NaBH_4$ and agitated at room temperature under $N_2$ for 30 minutes. The mixture is neutralized with glacial acetic acid, concentrated, taken up in ether, washed neutral with saturated NaCl solution, dried, and evaporated. The residue is dissolved in 140 ml. of pyridine, and the solution is combined with 80 ml. of acetic anhydride and agitated under $N_2$ for 1 hour at 80° C. After cooling, the mixture is introduced into ice water; the precipitate is filtered off and taken up in ether. The ether solution is washed neutral with saturated NaCl solution, dried, and evaporated. Recrystallization from methanol over carbon yields 61.0 g. of rac.-1,3-dimethoxy-17β-acetoxy-1,3,5(10),8,14-estrapentaene, m.p. 122°–124° C.

C:
1,3-Dimethoxy-17β-acetoxy-1,3,5(10),8-estratetraene 700 mg. pf rac.-1,3-dimethoxy-17β-acetoxy-1,3,5(10),8,14-estrapentaene in 10 ml. of distilled THF is hydrogenated over 200 mg. $Pd/CaCO_3$ (5%) at room temperature and under normal pressure until 46.6 ml. of $H_2$ has been absorbed. After the mixture has been filtered off from the catalyst, dried, and evaporated, 447 mg. of rac.-1,3-dimethoxy-17β-acetoxy-1,3,5(10),8-esratetraene is obtained from methanol, m.p. 111/112°–113° C.

With the use of 2-ethylcyclopentanedione-(1,3) and-/or 2-propylcyclopentanedione-(1,3) and further working up the reaction mixture according to (A), (B), and (C), the thus-obtained products are 1,3-dimethoxy-18-methyl-1,3,5(10),8,14-estrapentaen-17-one or
1,3-dimethoxy-18-ethyl-1,3,5(10),8,14-estrapentaen-17-one; and
1,3-dimethoxy-17β-acetoxy-18-methyl-1,3,5(10),8,14-estrapentaene or
1,3-dimethoxy-17β-acetoxy-18-ethyl-1,3,5(10),8,14-estrapentaene; and
1,3-dimethoxy-17β-acetoxy-18-methyl-1,3,5(10),8-estratetraene or
1,3-dimethoxy-17β-acetoxy-18-ethyl-1,3,5(10),8-estratetraene.

The following examples serve to explain the invention. The compounds of this invention are obtained as racemates as well as enantiomers. It is readily apparent to a person skilled in the art that the racemates can be separated into the enantiomers by separation methods generally known for the separation of optical antipodes. Therefore, this invention includes racemates and enantiomers.

Without further elaboration, it is believed that one skilled in the art can, using the preceding description, utilize the present invention to its fullest extent. The following preferred specific embodiments are, therefore, to be construed as merely illustrative, and not limitative of the remainder of the specification and claims in any way whatsoever.

EXAMPLE 1
rac.-1,3-Dimethoxy-8α-estra-1,3,5(10)-trien-17-one

In the presence of 0.15 g. of palladium/$CaCO_3$ (5%), 0.3 g. of rac.-1,3-dimethoxy-1,3,5(10),8,14-estrapentaen-17-one in 50 ml. of THF is hydrogenated within 17 hours at room temperature and under a hydrogen pressure of 50 atmosphere gauge. Then, the mixture is filtered off from the catalyst, the filtrate is concentrated by evaporation, and the residue is recrystallized from isopropyl ether, thus obtaining 40 mg. of final product, m.p. 158°–160°C.

EXAMPLE 2 rac.-1,3-Dimethoxy-17β-acetoxy-8α-estra-1,3,5(10)-triene a. 61 g. of rac.-1,3-dimethoxy-17β-acetoxy-1,3,5(10),8,14-estrapentaene in 400 ml. of benzene is hydrogenated in the presence of 14 g. of Raney nickel within 17 hours at room temperature and under a hydrogen pressure of 50 atmospheres gauge. The mixture is then filtered off from the catalyst, the filtrate is evaporated, and the residue is recrystallized from methanol over carbon, thus producing 50 g. of the above compound, m.p. 136°–138° C.

b. Under normal pressure and at room temperature, 100 mg. of rac.-1,3-dimethoxy-17β-acetoxy-1,3,5(10),8-estratetrene is hydrogenated in 1.4 ml. of distilled THF over 30 mg. of Pd/CaCO$_3$ (5%) until hydrogen is no longer absorbed. After filtration and evaporation, 44 mg. of final product is obtained from methanol, m.p. 126/130°–131° C.

Analogously, the following compounds are obtained:

rac.-1,3-dimethoxy-17β-acetoxy-18-methyl-8α-estra-1,3,5(10)-triene
rac.-1,3-dimethoxy-17β-acetoxy-18-ethyl-8α-estra-1,3,5(10)-triene.

EXAMPLE 3 rac.-1,3,17β-Triacetoxy-8α-estra-1,3,5(10)-triene

A mixture of 1 g. of rac.-1,3-dimethoxy-17β-acetoxy-8α-1,3,5(10)-triene and 10 g. of pyridine hydrochloride is heated under N$_2$ and agitation for 3 hours to 200°C. After cooling, the melt is dissolved in 50 ml. of pyridine and agitated with 5 ml. of acetic anhydride for 1 hour at room temperature and under N$_2$. After precipitation into ice water, the mixture is filtered off and worked up. The crude product is purified by gradient chromatography (methylene chloride/acetone = 9 ± 1), thus obtaining 930 mg. of final product, m.p. 146/147°–148° C.

Analogously, the following compounds are obtained:

rac.-1,3,17β-triacetoxy-18-methyl-8α-estra-1,3,5(10)-triene
rac.-1,3,17β-triacetoxy-18 -ethyl-8α-estra-1,3,5(10)-triene.

With the use of caproic anhydride and caprylic anhydride, respectively, in place of acetic anhydride, the following compounds are produced:

rac.-1,3,17β-tris(hexanoyloxy)-8α-estra-1,3,5(10)-triene
rac.-1,3,17β-tris(octanoyloxy)-8α-estra-1,3,5(10)-triene.

EXAMPLE 4 rac.-1,3-Dimethoxy-8α-estra-1,3,5(10)-trien-17β-ol 4.5 g. of rac.-1,3-dimethoxy-17β-acetoxy-8α-estra-1,3,5(10)-triene is saponified under N$_2$ in 100 ml. of methanol with 13 ml. of aqueous potash solution (10%) by heating for 1.5 hours under reflux. After cooling, the mixture is gently neutralized with glacial acetic acid, concentrated to half its volume, precipitated into ice water/NaCl, and worked up, thus obtaining 4.1 g. of crude product. By recrystallization of 500 mg. from methanol, 330 mg. of final product is obtained, m.p. 153/153.5°–154°C.

Analogously, the following compounds are produced:

rac.-1,3-dimethoxy-18-methyl-8α-estra-1,3,5(10)-trien-17β-ol
rac.-1,3-dimethoxy-18-ethyl-8α-estra-1,3,5(10)-trien-17β-ol.

EXAMPLE 5 rac.-1,3-Dimethoxy-17β-acetoxy-8α-estra-1,3,5(10)-triene

A solution of 60 mg. of rac.-1,3-dimethoxy-8α-estra-1,3,5(10)-trien-17-one in 3 ml. of ethanol and 1.0 ml. of THF is gradually combined at room temperature with 60 mg. of NaBH$_4$ and agitated for 30 minutes under N$_2$ and at room temperature. The reaction mixture is neutralized with glacial acetic acid, concentrated, taken up in ether, washed neutral with saturated NaCl solution, dried, and evaporated. The residue is dissolved in 1 ml. of pyridine, the solution is mixed with 0.5 ml. of acetic anhydride and maintained for 1 hour at 80° C. under N$_2$. After cooling, the mixture is introduced into ice water; the precipitate is filtered off and taken up in ether. The ether solution is washed neutral with saturated NaCl solution, dried, and evaporated. Recrystallization from methanol over carbon yields 42 mg. of product, m.p. 131°–134° C.

EXAMPLE 6 rac.-1,3-Dimethoxy-17α-ethinyl-8α-estra-1,3,5(10)-trien-17β-ol

An autoclave is charged with 1.2 g. of potassium tert.butylate (10 millimoles), 2.5 ml. of tert.-butanol, and 20 ml. of absolute THF; the vessel is purged with nitrogen and filled up with acetylene to 4.5 atmospheres gauge. After 30 minutes, 740 mg. of rac.-1,3-dimethoxy-8α-estra-1,3,5(10)-trien-17-one in 5 ml. of absolute THF is added, and the mixture is allowed to react for 45 minutes under acetylene pressure. The mixture is then precipitated into 40 ml. of dilute sulfuric acid (20% strength) and ice, extracted with methylene chloride, and worked up. The crude product is purified by column chromatography, thus obtaining 430 mg. of final product from hexane/acetone, m.p. 177/178°–179° C.

Analogously, but without the use of tert.-butanol as the solvent during the ethinylation, the following compounds are obtained:

rac.-1,3-dimethoxy-18-methyl-17α-ethinyl-8α-estra-1,3,5(10)-trien-17β-ol
rac.-1,3-dimethoxy-18-ethyl-17α-ethinyl-8α-estra-1,3,5(10)-trien-17β-ol.

EXAMPLE 7 rac.-1,3-Diacetoxy-8α-estra-1,3,5(10)-trien-17-one

A mixture of 25 g. of pyridine hydrochloride and 2.5 g. of 1,3-dimethoxy-8α-estra-1,3,5(10)-trien-17-one is heated to 200° C. under N$_2$ and agitation for 3 hours. After cooling, adding 120 ml. of pyridine and 12 ml. of acetic anhydride to the mixture, and agitating for 1 hour at room temperature, the solution is introduced into ice water/NaCl, stirred for one-half hour, filtered off, and worked up. The crude product (2.5 g.) is purified by gradient chromatography (60 g. of SiO$_2$; methylene chloride/10% acetone), thus obtaining, after recrystallization from methanol, 710 mg. of final product, m.p. 179°–180.5° C.

EXAMPLE 8 rac.-1,3-Diacetoxy-17α-ethinyl-8α-estra-1,3,5(10)-trien-17β-ol

A mixture of 8.3 g. of potassium tert.-butylate, 2.5 ml. of tert.-butanol, and 20 ml. of absolute THF is agitated for 1 hour at room temperature in a tumbling bomb tube after purging with N$_2$ under acetylene. Thereafter, 740 mg. of rac.-1,3-diacetoxy-8α-estra-1,3,5(10)-trien-17-one in 5 ml. of absolute THF is added thereto, and the tumbling is carried out for 2 hours under acetylene at room temperature. The mixture is introduced into 40 ml. of dilute sulfuric acid (20%), filtered off, and worked up. The crude product is after-acetylated in 5 ml. of pyridine with 2 ml. of acetic anhydride. After precipitating the mixture in water and working up, the crude product (850 mg.) is purified by gradient chromatography (20 g. of SiO$_2$, hexane/25% acetone), obtaining 152 mg. of final product, m.p. 154°–155° C.

Analogously, but without tert.-butanol as the solvent during the ethinylation, the following compounds are produced:

rac.-1,3-diacetoxy-18-methyl-17α-ethinyl-8α-estra-1,3,5(10)-trien-17β-ol
rac.-1,3-diacetoxy-18-ethyl-17α-ethinyl-8α-estra-1,3,5(10)-trien-17β-ol.

EXAMPLE 9

1,3-Diacetoxy-8α-estra-1,3,5(10)-trien-17-one

A suspension of 42 g. of 3-hydroxy-8α-estra-1,3,5(10)-trien-17-one in 500 ml. of glacial acetic acid is combined with 120 g. of lead tetraacetate; the mixture is then agitated for 3 minutes at room temperature under exclusion of moisture and then poured into 600 ml. of ice water. The precipitate is filtered, washed with water, and the filter residue taken up in methylene chloride. The solution of the substance is washed neutral with sodium bicarbonate solution and water, dried, and concentrated. The concentrate is filtered with methylene chloride over 400 g. of silica gel (+ 10% water). The fractions containing the substance are combined and freed of solvent, thus obtaining 7 g. of 10β-acetoxy-8α-estra-1,4-diene-3,17-dione as an oil.

A suspension of 13.0 g. of 10β-acetoxy-8α-estra-1,4-diene-3,17-dione in 125 ml. of acetic anhydride is mixed dropwise with 0.7 ml. of concentrated sulfuric acid and stirred for 3 hours at room temperature, thus gradually dissolving the substance. The mixture is then introduced into 10 times the amount of ice water to which is added 7 g. of sodium carbonate. The mixture is agitated for 1 hour and then filtered off. The washed and dried residue is recrystallized from methanol, thus obtaining 7 g. of final product, m.p. 208°–211° C. $[\alpha]_D^{20} = +89°$ (CHCl$_3$, c = 0.5).

Analogously, the following compound is obtained:
1,3-diacetoxy-18-methyl-8α-estra-1,3,5(10)-trien-17-one, m.p. 132°–133° C (from methanol).

EXAMPLE 10

1,3,17β-Triacetoxy-8α-estra-1,3,5(10)-triene

A solution of 6 g. of 1,3-diacetoxy-8α-estra-1,3,5(10)-trien-17-one in 240 ml. of methanol and 100 ml. of THF is gradually combined at room temperature with 600 mg. of NaBH$_4$ and stirred for 30 minutes at room temperature under N$_2$. The mixture is neutralized with glacial acetic acid and then acetylated and worked up in accordance with Example 5. Yield: 4.8 g., m.p. 149/150°–151° C. $[\alpha]_D^{20} = +4.2°$ (CHCl$_3$, c = 0.5).

Analogously, the following compound is produced: 1,3,17β-triacetoxy-18-methyl-8α-estra-1,3,5(10)-triene.

EXAMPLE 11

1,3-Diacetoxy-17α-ethinyl-8α-estra-1,3,5(10)-trien-17β-ol 750 mg. of 1,3-diacetoxy-8α-estra- 1,3,5(10)-trien-17-one is ethinylated and worked up in accordance with Example 8. Yield: 230 mg. of a foam which does not crystallize, $[\alpha]_D^{20} = -33.8°$ (CHCl$_3$, c = 0.5).

Analogously, the following substance is obtained: 1,3-diacetoxy-18-methyl- 17α-ethinyl-8α-estra-1,3,5(10)-trien-17β-ol.

EXAMPLE 12

1,3-Bis(cyclopentyloxy)-8α-estra-1,3,5(10)-trien-17β-ol

A solution of 850 mg. of 8α-estra-1,3,5(10)-triene-1,3,17β-triol (prepared from compound of Example 10 by saponification in 30 ml. of ethanol is heated to the boiling point under N$_2$ with 2.5 ml. of cyclopentyl bromide and 2.5 g. of potassium carbonate for 5 hours. The mixture is then introduced into ice water, taken up in ether, and the organic phase is washed, dried, and evaporated. After purification by chromatography on silica gel, 365 mg. of final product is obtained.

EXAMPLE 13

1,3-Bis(butoxy)-8α-estra-1,3,5(10)-trien-17β-ol

Analogously to Example 12, 500 mg. of 8α-estra-1,3,5(10)-triene-1,3,17β-triol is reacted with 1.5 ml. of n-butyl bromide and worked up. Yield: 230 mg.

EXAMPLE 14

1,3,17β-Tris(tetrahydropyranyloxy)-8α-estra-1,3,5(10)-triene

A solution of 800 mg. of 8α-estra-1,3,5(10)-triene-1,3,17β-triol in 40 ml. of absolute benzene is combined with 1.4 ml. of distilled dihydropyran and 10 mg. of p-toluenesulfonic acid. The solution is stirred for 1.5 hours at room temperature and then washed neutral with sodium bicarbonate solution and water, dried, and evaporated; yield: 700 mg. of a crude product.

EXAMPLE 15

1,3,17β-Tris(hexanoyloxy)-8α-estra-1,3,5(10)-triene

A solution of 450 mg. of 8α-estra-1,3,5(10)-triene-1,3,17β-triol in 3 ml. of pyridine is combined with 1.5 ml. of caproic anhydride and heated under nitrogen to 90° C. for 5 hours. The mixture is then poured into ice water, a small amount of methanol is added, and the mixture is stirred for 1 hour to decompose excess anhydride. The mixture is taken up in ether, the ether solution is washed neutral with dilute sulfuric acid, sodium bicarbonate solution, and water, dried, and evaporated. After purification by chromatography over silica gel, 320 mg. of final product is obtained.

EXAMPLE 16

1,3-Dimethoxy-17α-chloroethinyl-8α-estra-1,3,5(10)-trien-17β-ol

A methyllithium solution is prepared from 1.39 g. of lithium and 6.9 ml. of methyl iodide in 50 ml. of absolute ether by refluxing (45 minutes under $N_2$). After cooling to 0° C, 3.75 ml. of dichloroethylene in 15 ml. of absolute ether is added dropwise. Afer agitating the reception mixture for 1.5 hours at room temperature, a solution of 1.3 g. of 1,3-dimethoxy-8α-estra-1,3,5(10)-trien-17-one in 50 ml. of THF is added within 30 minutes, and the mixture is heated to the boiling point for 1 hour. Then, saturated sodium chloride solution is added under ice cooling, the mixture is diluted with ether, washed neutral, dried, and evaporated. After purification over silica gel, 475 mg. of final product is obtained.

EXAMPLE 17

1,3-Diacetoxy-8α-estra-1,3,5(10)-trien-17β-ol

A solution of 1 g. of 1,3-diacetoxy-8α-estra-1,3,5(10)-trien-17-one in 30 ml. of absolute THF is agitated under ice cooling with 2 g. of lithium tri-tert.-butoxyaluminum hydride for 45 minutes under ice cooling. The mixture is then introduced into acetic ice water/NaCl and extracted with ether. The organic phase is washed neutral, dried, and evaporated. The residue (1 g.) is purified by layer chromatography; after recrystallization from hexane/acetone, 380 mg. of 1,3-diacetoxy-8α-estra-1,3,5(10)-trien-17β-ol is produced, m.p. 210°–211° C.

EXAMPLE 18

1,3-Dihydroxy-8α-estra-1,3,5(10)-trien-17-one

A solution of 3 g. of 1,3-diacetoxy-8α-estra-1,3,5(10)-trien-17-one in 9 ml. of methylene chloride and 18 ml. of methanol is combined at 0° C. and under nitrogen with 0.23 ml. of perchloric acid (70%) in 1 ml. of methanol; the mixture is then agitated for 3 days at room temperature. Then, the mixture is diluted with ethyl acetate and washed neutral with saturated sodium chloride solution. After drying and evaporation, 2.9 g. of 1,3-dihydroxy-8α-estra-1,3,5(10)-trien-17-one is obtained as an oily substance.

EXAMPLE 19

1,3-Bis(mesyloxy)-8α-estra-1,3,5(10)-trien-17-one

A solution of 1 g. of 1,3-dihydroxy-8α-estra-1,3,5(10)-trien-17-one (prepared from compound of Example 9 by saponification) in 14 ml. of pyridine is combined at 0° C. with 1.9 ml. of methanesulfonic acid chloride and agitated for 3 days at 0°–10° C. The mixture is then introduced into ice water (acidified with HCl), filtered off, and the residue dissolved in methylene chloride. After chromatography on $SiO_2$, 800 mg. of 1,3-bis(mesyloxy)-8α-estra-1,3,5(10)-trien-17-one is obtained.

EXAMPLE 20

1,3-Bis(mesyloxy)-8α-estra-1,3,5(10)-trien-17β-ol

A solution of 400 mg. of 1,3-bis(mesyloxy)-8α-estra-1,3,5(10)-trien-17-one in 10 ml. of absolute THF is combined with 800 mg. of lithium tri-tert.-butoxyaluminum hydride, and the mixture is agitated for 60 minutes at 0° C. Then, the mixture is neutralized with glacial acetic acid and extracted with ethyl acetate. The organic phase is washed with water, dried, and evaporated. The thus-obtained crude product (400 mg.) is purified by layer chromatography, thus obtaining 320 mg. of 1,3-bis(mesyloxy)-8α-estra-1,3,5(10)-trien-17β-ol.

EXAMPLE 21

1,3-Bis(mesyloxy)-17β-acetoxy-8α-estra-1,3,5(10)triene

A solution of 200 mg. of 1,3-bis(mesyloxy)-8α-estra-1,3,5(10)-trien-17β-ol in 3 ml. of pyridine is combined with 2 ml. of acetic anhydride and allowed to stand at room temperature for 3 days. Then, the mixture is introduced into ice water, extracted with methylene chloride, washed with water, dried, and evaporated. The residue (180 mg.) is purified by layer chromatography, thus obtaining 150 mg. of 1,3-bis(mesyloxy)-17β-acetoxy-8α-estra- 1,3,5(10 0-triene.

EXAMPLE 22

1,3,17β-Tris(mesyloxy)-17α-ethinyl-8α-estra-1,3,5(10)-triene

At −10° C., acetylene is introduced for 60 minutes into a suspension of 1.2 g. of potassium tert.-butylate in 20 ml. of absolute THF. The thus-prepared suspension of potassium acetylide is combined with a solution of 400 mg. of 1,3-diacetoxy-8α-estra-1,3,5(10)-trien-17-one in 8 ml. of absolute THF. Under agitation, acetylene is further introduced for 1.5 hours at −10° C., and then the mixture is neutralized by adding glacial acetic acid. The mixture is introduced into ice water and extracted with ether. The ether solution is washed with water, dried, and evaporated. The thus-obtained crude product (250 mg.) is dissolved in 5 ml. of pyridine, combined at 0° C. with 1 ml. of methanesulfonic acid chloride, and stirred for 3 days at 0°–10° C. The mixture is then introduced into ice water (acidified with HCl), filtered off, and the residue is dissolved in methylene chloride. After chromatography on $SiO_2$, 250 mg. of 1,3,17β-tris(mesyloxy)-17α-ethinyl-8α-estra-1,3,5(10)-triene is obtained.

EXAMPLE 23

1,3-Bis(p-tosyloxy)-8α-estra-1,3,5(10)-trien-17-one

A solution of 1 g. of 1,3-dihydroxy-8α-estra-1,3,5(10)-trien-17-one in 14 ml. of pyridine is combined at 0° C. with 2.5 g. of p-toluenesulfonic acid chloride and stirred for 3 days at 0°–10° C. The mixture is then introduced into ice water (acidified with HCl), filtered off, and the residue is dissolved in methylene chloride. Chromatography on silica gel yields 820 mg. of 1,3-bis(p-tosyloxy)-8α-estra-1,3,5(10)-trien-17-one.

EXAMPLE 24

1,3-Bis(diethylaminosulfonyloxy)-8α-estra-1,3,5(10)-trien-17-one

A solution of 250 mg. of 1,3-dihydroxy-8α-estra-1,3,5(10)-trien-17-one in 6.5 ml. of dimethyl sulfoxide is mixed under cooling and nitrogen with 250 mg. of NaH (50% suspension in oil), and agitated for 30 minutes at room temperature. A solution of 1.05 g. of diethylaminosulfonyl chloride in 2 ml. of dimethyl sulfoxide is then added to the mixture, and the latter is agitated for 25 hours at room temperature. The mixture is introduced into acetic ice water (NaCl), the organic substances are extracted with ether, and the extracts are washed, dried, and evaporated. After purification by chromatography, 150 mg. of 1,3-bis(diethylaminosulfonyloxy)-8α-estra-1,3,5(10)-trien-17-one is produced.

EXAMPLE 25

1,3-Bis(piperidinosulfonyloxy)-8α-estra-1,3,5(10)-trien-17-one

The above compound is prepared from 1,3-dihydroxy-8α-estra-1,3,5(10)-trien-17-one by reaction with piperidinosulfonyl chloride analogously to Example 24.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1,3-oxygenated 8α-estratriene of the formula

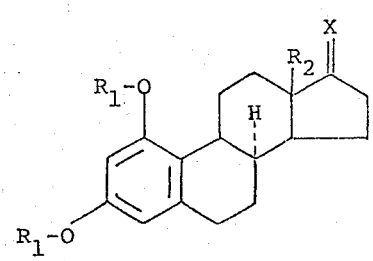

wherein X is an oxygen atom or

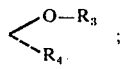

$R_1$ and $R_3$ each are a hydrogen atom, hydrocarbon carbonyl or sulfonyl of 1–15 carbon atoms, alkyl of 1–5 carbon atoms, cycloalkyl of 3–8 ring carbon atoms, or tetrahydropyranyl; $R_2$ is alkyl of 1–4 carbon atoms; and $R_4$ is a hydrogen atom alkyl of 1–6 carbon atoms or chloroethinyl.

2. A compound of claim 1, wherein X is

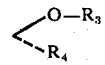

$R_1$ and $R_3$ each are hydrogen atoms, alkyl of 1–4 carbon atoms or alkanoyl of 2–8 carbon atoms and $R_4$ is a hydrogen atom.

3. A compound of claim 1, 1,3-dimethoxy-8α-estra-1,3,5(10)-trien-17-one.
4. A compound of claim 1, 1,3-dimethoxy-17β-acetoxy-8α-estra-1,3,5(10)-triene.
5. A compound of claim 1, 1,3,17β-triacetoxy-8α-estra-1,3,5(10)-triene.
6. A compound of claim 1, 1,3-dimethoxy-8α-estra-1,3,5(10)-trien-17β-ol.
7. A compound of claim 1, 1,3-diacetoxy-8α-estra-1,3,5(10)-trien-17-one.
8. A compound of claim 1, 1,3-bis(cyclopentyloxy)-8α-estra-1,3,5(10)-trien-17β-ol.
9. A compound of claim 1, 1,3-bis(butoxy)-8α-estra-1,3,5(10)-trien-17β-ol.
10. A compound of claim 1, 1,3,17β-tris(tetrahydropyranyloxy)-8α-estra-1,3,5(10)-triene.
11. A compound of claim 1, 1,3,17β-tris(hexanoyloxy)-8α-estra-1,3,5(10)-triene.
12. A compound of claim 1, 1,3-dimethoxy-17α-chloroethinyl-8α-estra-1,3,5(10)-trien-17β-ol.
13. A compound of claim 1, 1,3-diacetoxy-8α-estra-1,3,5(10)-trien-17β-ol.
14. A compound of claim 1, 1,3-dihydroxy-8α-estra-1,3,5(10)-trien-17-one.
15. A compound of claim 1, 1,3-bis(mesyloxy)-8α-estra-1,3,5(10)-trien-17-one.
16. A compound of claim 1, 1,3-bis(mesyloxy)-8α-estra-1,3,5(10)-trien-17β-ol.
17. A compound of claim 1, 1,3-bis(mesyloxy)-17β-acetoxy-8α-estra-1,3,5(10)-triene.
18. A compound of claim 1, 1,3,17β-tris(mesyloxy)-17α-ethinyl-8α-estra-1,3,5(10)-triene.
19. A compound of claim 1, 1,3-bis(p-tosyloxy)-8α-estra-1,3,5(10)-trien-17-one.
20. 1,3-Bis(diethylaminosulfonyloxy)-8α-estra-1,3,5(10)-trien-17-one.
21. 1,3-Bis(piperidinosulfonyloxy)-8α-estra-1,3,5(10)-trien-17-one.
22. A pharmaceutical composition comprising a compound of claim 1 in admixture with a pharmaceutically acceptable carrier.
23. A compound of claim 1, wherein X is an oxygen atom.
24. A compound of claim 1, wherein each $R_1$ is a hydrogen atom.

* * * * *